United States Patent
Barias et al.

(10) Patent No.: US 12,162,825 B2
(45) Date of Patent: Dec. 10, 2024

(54) ETHERIFICATION OF HIGH CONCENTRATION C5 ISO-OLEFINS VIA CATALYTIC DISTILLATION

(71) Applicant: LUMMUS TECHNOLOGY LLC, Houston, TX (US)

(72) Inventors: Rosette Barias, Houston, TX (US); Michael Jon Scott, Houston, TX (US)

(73) Assignee: Lummus Technology LLC, Houston, TX (US)

( * ) Notice: Subject to any disclaimer, the term of this patent is extended or adjusted under 35 U.S.C. 154(b) by 484 days.

(21) Appl. No.: 17/650,788

(22) Filed: Feb. 11, 2022

(65) Prior Publication Data

US 2022/0259126 A1 Aug. 18, 2022

Related U.S. Application Data

(60) Provisional application No. 63/149,118, filed on Feb. 12, 2021.

(51) Int. Cl.
*C07C 41/06* (2006.01)
*C07C 41/05* (2006.01)
*C07C 41/42* (2006.01)

(52) U.S. Cl.
CPC .............. *C07C 41/06* (2013.01); *C07C 41/05* (2013.01); *C07C 41/42* (2013.01)

(58) Field of Classification Search
CPC ................................ C07C 41/06; C07C 41/42
See application file for complete search history.

(56) References Cited

U.S. PATENT DOCUMENTS

| | | | |
|---|---|---|---|
| 4,950,803 A | 8/1990 | Smith, Jr. et al. | |
| 5,245,087 A | 9/1993 | Zahn | |
| 5,321,163 A | 6/1994 | Hickey et al. | |
| 5,348,707 A * | 9/1994 | Harandi ........... | C07C 41/42 |
| | | | 422/129 |
| 5,919,989 A | 7/1999 | Bakshi et al. | |
| 6,232,509 B1 | 5/2001 | Smith, Jr. et al. | |
| 6,262,314 B1 | 7/2001 | Escalante et al. | |
| 7,553,995 B2 | 6/2009 | Boyer et al. | |
| 7,732,648 B2 | 6/2010 | Bakshi | |

FOREIGN PATENT DOCUMENTS

| | | |
|---|---|---|
| EP | 0850906 B1 | 4/2001 |
| WO | 9203401 A1 | 3/1992 |

OTHER PUBLICATIONS

International Preliminary Report on Patentability issued in Application No. PCT/US2022/016184, mailed on Aug. 15, 2023 (7 pages).

* cited by examiner

*Primary Examiner* — Rosalynd A Keys
(74) *Attorney, Agent, or Firm* — Osha Bergman Watanabe & Burton LLP

(57) ABSTRACT

Systems and processes for the efficient conversion of high concentration isoolefin streams to tertiary alkyl ethers are disclosed. The systems and processes may include a feed system to advantageously divide the high concentration isoolefin feed to multiple fixed bed reactors and a catalytic distillation reactor to control the reaction exotherm and achieve a high isoolefin conversion.

7 Claims, 3 Drawing Sheets

ETHERIFICATION OF HIGH CONCENTRATION C5 ISO-OLEFINS VIA CATALYTIC DISTILLATION

FIELD OF THE DISCLOSURE

Embodiments of the present disclosure generally relate to the production of tertiary alkyl ethers. More specifically, embodiments disclosed herein relate to the production of tertiary amyl methyl ether (TAME), tertiary amyl ethyl ether (TAEE) or other tertiary amyl alkyl ethers from feedstocks that contain a relatively high concentration of isoamylene.

BACKGROUND

Various processes have been proposed to produce tertiary alkyl ethers from various hydrocarbon feedstocks, such as those containing isobutylene, isoamylene, or a mixture thereof. For example, U.S. Pat. Nos. 4,950,803, 5,321,163, 6,232,509, and 7,553,995 each disclose processes for conversion of isoolefins to tertiary ethers using a catalytic distillation reactor. The typical feedstocks described in these applications are light naphtha cuts or C4/C5 cuts from fluid catalytic cracking or steam cracking units, where such feeds typically have a relatively low amount of isoolefins, such as less than 35 weight percent etherifiable olefins, as described in U.S. Pat. No. 7,553,995.

U.S. Pat. No. 4,950,803 describes the use of a boiling point reactor to control the exothermic reaction and the excess heat in the reactor. Also noted in the background are the use of heat exchangers in liquid phase reactors to control the excess heat. Typical conversions noted in the '803 patent are 80-90% for a feed stream containing 5 to 30 wt % isoolefins, and lower for streams containing higher concentrations of the isoolefins.

SUMMARY OF THE CLAIMED EMBODIMENTS

As described above, the effects of excess heat from the exothermic reaction result in typically lower than desirable conversion of isoolefins in a stream containing a high concentration of the isoolefin. In contrast, the present inventors have developed embodiments herein that may be used to convert isoolefins to tertiary alkyl ethers at high conversion, such as greater than 90%, even for feedstocks having a relatively high concentration of isoolefin, such as feedstocks having greater than 50% isoamylene.

In one aspect, embodiments disclosed herein relate to processes for producing tertiary amyl alkyl ether. The processes may include providing a mixed hydrocarbon feed containing a mixture of C5 hydrocarbons. The mixed hydrocarbon feed contains greater than 50 wt % isoamylene. The mixed hydrocarbon feed is then divided into three portions, either before or after alcohol addition. The three resulting portions may include a first isoamylene feed portion, a second isoamylene feed portion, and a third isoamylene feed portion. The first isoamylene feed portion, alcohol, and a first portion of a first reactor effluent are fed to a first reactor, wherein the alcohol is reacted with isomaylene over an etherification catalyst to form tertiary amyl alkyl ether. A first reactor effluent is recovered from the first reactor and the first reactor effluent is divided into the first portion of the first reactor effluent and a second portion of the first reactor effluent. The first portion of the first reactor effluent is recycled to the first reactor, and mixed with the incoming feed, as noted above. The second portion of the first reactor effluent, alcohol, and the second isoamylene feed portion are fed to a second reactor, wherein the alcohol is reacted with isomaylene over an etherification catalyst to form tertiary amyl alkyl ether. A second reactor effluent is recovered from the second reactor and the second reactor effluent, alcohol, and the third isoamylene feed portion are then fed to a catalytic distillation column. In the catalytic distillation column, isoamylene and alcohol are reacted over an etherification catalyst to form tertiary amyl alkyl ether, and concurrently the tertiary amyl alkyl ether is separated from unreacted alcohol, unreacted isoamylene, and other C5 hydrocarbons contained in the mixed hydrocarbon feed. The tertiary amyl alkyl ether is recovered from the catalytic distillation column as a bottoms fraction, and the unreacted alcohol, unreacted isoamylene, and other C5 hydrocarbons contained in the mixed hydrocarbon feed are recovered as an overheads fraction.

In some embodiments, the processes may include maintaining isoamylene in a total feed to the first reactor at a concentration of less than 28 wt %. Similarly, some embodiments may include maintaining isoamylene in a total feed to the second reactor at a concentration of less than 28 wt %.

In some embodiments, the processes may include mixing a stoichiometric amount of alcohol, +/−15% relative to the isoamylene, with the mixed hydrocarbon feed prior to dividing the feed into multiple portions. In other embodiments, the processes may include mixing an alcohol feed stream and an alcohol recycle stream with the mixed feed stream prior to separating the mixed feed stream into the three portions.

Processes according to some embodiments may include separating the overheads fraction to recover an alcohol recycle fraction and a hydrocarbon raffinate fraction. The alcohol recycle may be combined with the mixed feed, or may be recycled to one or more of the first reactor, the second reactor, and the catalytic distillation column.

In another aspect, embodiments disclosed herein relate to systems for producing tertiary amyl alkyl ether. The systems may include a flow line for providing a mixed hydrocarbon feed containing a mixture of C5 hydrocarbons. The mixed hydrocarbon feed may contain greater than 50 wt % isoamylene. The system may also include a flow line for providing an alcohol feed, such as a C1 to C6 primary or secondary alcohol. A system may be provided for mixing the alcohol feed and the mixed hydrocarbon feed to form a mixed feed, where the system for mixing may include a mixing vessel, a mixing tee, or combinations thereof, among other systems for mixing known in the art. A system may also be provided for dividing the mixed feed into three portions, such as a system of tees and valves to direct and control flow. The three mixed feed portions may include a first mixed feed portion, a second mixed feed portion, and a third mixed feed portion. Fluid connected to the system for dividing may be a flow line for mixing and feeding the first mixed feed portion and a first portion of a first reactor effluent to a first reactor. The first reactor may be configured for reacting the alcohol with isomaylene over an etherification catalyst to form tertiary amyl alkyl ether and for recovering a first reactor effluent. A flow system may be provided for dividing the first reactor effluent into the first portion of the first reactor effluent and a second portion of the first reactor effluent. A flow line for recycling the first portion of the first reactor effluent may be connected to the flow line for mixing. Further, a flow line may be provided for feeding the second portion of the first reactor effluent and the second mixed feed portion to a second reactor. The second reactor may be configured for reacting the alcohol with isomaylene over an etherification catalyst to form tertiary amyl alkyl ether and for recovering a second reactor effluent. A flow line may be provided for feeding the second reactor effluent and the third mixed feed portion to a catalytic distillation column. The catalytic distillation column may be configured for: reacting isoamylene and alcohol over an etherification catalyst to form tertiary amyl alkyl ether; separating the tertiary amyl alkyl ether from unreacted alcohol, unreacted isoamylene, and other C5 hydrocarbons contained in the mixed hydrocarbon feed; recovering the tertiary amyl alkyl ether from the catalytic distillation column as a bottoms fraction, and recovering the unreacted alcohol, unreacted isoamylene, and other C5 hydrocarbons contained in the mixed hydrocarbon feed as an overheads fraction.

In some embodiments, the systems may further include a control system for maintaining isoamylene in a total feed to the first reactor at a concentration of less than 28 wt %. Similarly, some embodiments of the systems may include a control system for maintaining isoamylene in a total feed to the second reactor at a concentration of less than 28 wt %.

The systems may also include an alcohol recovery system for separating the overheads fraction to recover an alcohol recycle fraction and a hydrocarbon raffinate fraction, as well as a flow line for feeding the alcohol recycle fraction to the system for mixing the alcohol feed.

Other aspects and advantages will be apparent from the following description and the appended claims.

Figure 1:
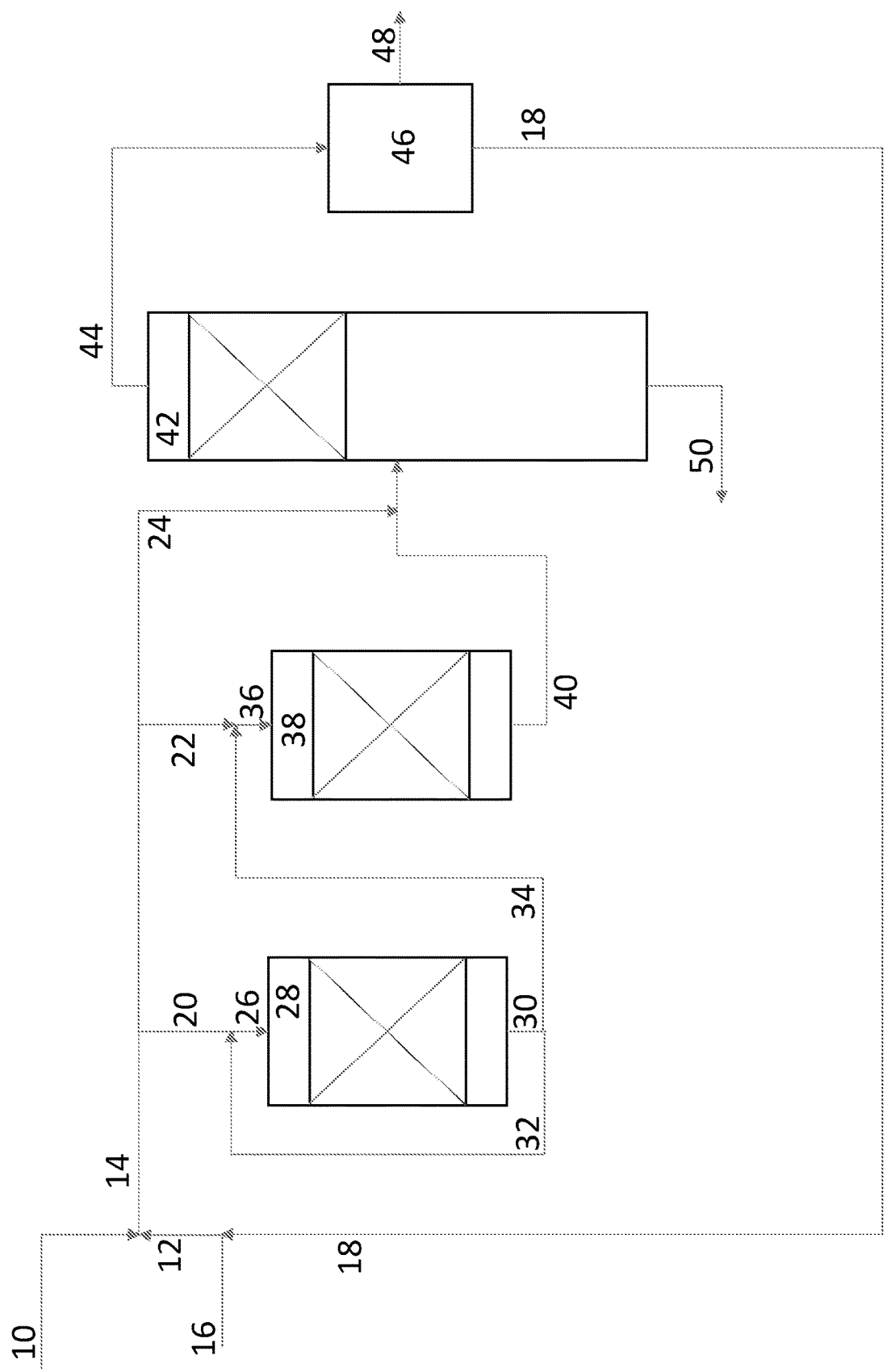
FIG. 1 is a simplified flow diagram of a process according to one or more embodiments disclosed herein.

The simplified flow diagrams illustrate primary unit operations and flow streams associated with and for the understanding of embodiments herein. One skilled in the art would recognize that auxiliary equipment, such as pumps, valves, utilities, reboilers, overhead condensers, and control systems, among other items necessary for operation, are not illustrated for purposes of simplifying the flow diagrams presented and described herein.

DETAILED DESCRIPTION

Embodiments of the present disclosure generally relate to the production of tertiary alkyl ethers. More specifically, embodiments disclosed herein relate to the production of tertiary amyl methyl ether (TAME), tertiary amyl ethyl ether (TAEE) or other tertiary amyl alkyl ethers from feedstocks that contain a relatively high concentration of isoamylene.

Feedstocks that may be used in embodiments herein may contain a wide number of hydrocarbons, and may include a mixture of C5 hydrocarbons, a mixture of C4 and C5 hydrocarbons, and a mixture of C4-C6 hydrocarbons, among other mixtures, such as C5+C6, C5-C7, C4-C7, C4-C8, and C5-C8, among others. The feedstock may contain, as a primary component (present at the highest concentration of the various hydrocarbons), or as a majority component (present at greater than 50 wt % in the mixed feedstock) isoamylene. Isoamylene containing feedstocks may include greater than 40 wt %, greater than 45 wt %, greater than 50 wt %, greater than 55 wt %, greater than 60 wt %, greater than 65 wt %, or greater than 70 wt % isoamylene. For example, isoamylene containing feedstocks may contain isoamylene at a concentration within a range having a lower limit of 40 wt %, 45 wt %, 50 wt %, 55 wt %, or 60 wt % to an upper limit of 50 wt %, 55 wt %, 60 wt %, 65 wt %, 70 wt %, or 75 wt %, where any lower limit may be combined with any upper limit. The remaining components may include one or more hydrocarbons, including paraffins, olefins, and/or dienes, as may result from various upstream processes.

Prior to feed of the isoolefin feedstocks to the etherification reactors, the isoolefin feedstocks may be treated to reduce a diene content to acceptable levels, such as less than 1000 ppm diene. For example, a mixed C5 hydrocarbon stream containing pentadiene may be selectively hydrogenated to reduce the content of the pentadiene to acceptable levels to avoid color and/or odor issues in the tertiary alkyl ether product recovered.

While described herein with respect to isoamylene containing streams, embodiments herein may also be useful for other isoolefin containing streams, such as those containing isobutylene, isohexene, or other isoolefins, where the isoolefins are contained in the feed stream at a relatively high concentration level.

The isoolefins (isoamylene) may be reacted with an alcohol in the presence of an etherification catalyst. Any catalyst typically used in etherification processes may be used in embodiments disclosed herein. Conventional cation exchange resins and/or zeolites may be used in various embodiments. The alcohol may be a C1 to C6 alcohol, such as methanol, ethanol, and/or propanol, among others. The alcohols may be used individually (e.g., only methanol or only ethanol) or may be used in admixture of two or more alcohols (e.g., a mixture of methanol and ethanol).

The alcohol, such as methanol, may be fed to reactors herein at a stoichiometric amount with respect to the isoolefin (isoamylene) present. In some embodiments, an excess of up to 10% or 15% alcohol may be used. In other embodiments, less than a stoichiometric amount of alcohol may be employed.

In one or more embodiments, processes for the conversion of isoolefins (isoamylene) to tertiary alkyl ethers (tertiary amyl alkyl ether) may include introducing a mixed hydrocarbon feed, such as a C5 feed containing greater than 60 wt % isoamylenes, along with a proportional amount of methanol, to a fixed bed reactor section wherein the bulk of the etherification of the reactive isoamylenes occurs. The alcohol may be combined with the mixed hydrocarbon feed or may be fed directly to the reactors and CD column. In some embodiments, the alcohol is combined with the mixed hydrocarbon feed, and the hydrocarbon-alcohol mixture may then be split into multiple portions of equal composition for feed to the reactors (Primary, Secondary, CD Column) as desired. Mixing the totality of the feed may be simpler, providing for one control loop to provide a mixed feed having a desired ratio of isoolefin to alcohol, rather than multiple control loops and feed systems for controlling the desired ratio of isoolefin to alcohol for each individual reactor.

The mixed feed may be split into two or more portions, with a portion of the feed being fed to a first fixed bed reactor (Primary Reactor) for conversion therein, and a portion of the feed bypassing the Primary Reactor. In the Primary Reactor, the mixed feed is diluted with recycled effluent from the outlet of the Primary Reactor before being fed to the Primary Reactor. The dilution of the isoamylene in the feed allows for control over the exotherm across the reactor and the conversion of isoamylene to ether product therein.

The effluent of the Primary Reactor is split, with a portion recycled back to the inlet of the reactor to dilute the feed, as noted above, and a portion sent to a second fixed bed reactor (Secondary Reactor) for further conversion. The Secondary Reactor feed stream may be a portion of the effluent recovered from the Primary Reactor. Optionally, the portion of the effluent recovered from the Primary Reactor may be combined with a portion of the mixed feed that bypassed the Primary Reactor. In this manner, a diluted concentration of isoamylene in the feed to the Secondary Reactor may be maintained, similar to the Primary Reactor inlet. The feed to the Secondary Reactor then undergoes etherification over an etherification catalyst contained in the Secondary Reactor.

The outlet of the Secondary Reactor, along with any remaining portion of the mixed feed that bypasses the Primary and Secondary Reactor, may be fed to a Catalytic Distillation (CD) column wherein a catalytic section containing an etherification catalyst resides. The mixed feed may be introduced, for example, to a feed tray of the CD column located below the catalytic section. In the CD column, a portion of the remaining isoamylene (unreacted in the Primary or Secondary Reactors and/or from the feed bypass) reacts with the alcohol and the reaction products are concurrently fractionated, recovering a bottoms fraction, containing the tertiary alkyl ether, and an overheads fraction, containing any unreacted isoolefin, any unreacted alcohol, and any other lighter components contained in the mixed hydrocarbon feedstock.

The bottoms of the CD Column may then be cooled and recovered as a purified ethers product. The overheads fraction may be condensed, a portion used to reflux the column, the remainder being forwarded to an alcohol recovery zone to separate any unreacted alcohol from the inert and unreacted hydrocarbons, such as n-pentane, isopentane, and other hydrocarbons contained in the mixed hydrocarbon feed. The recovered alcohol may be recycled to the reactors for further reaction with isoolefins.

In some embodiments, an optional Finishing Reactor containing etherification catalyst may be included in the process, further converting unreacted isoolefin and alcohols in the overheads fraction, to maximize the production of the ether product, if desired.

By splitting the isoolefin feedstock for feed to multiple fixed bed reactors and a CD column, as described above, the reaction exotherm may be effectively controlled and a high conversion of the isoolefin may be achieved. For example, some embodiments herein may result in conversion of greater than 90% of the isoolefin (isoamylene), greater than 92% of the isoolefin, greater than 94% of the isoolefin, or even greater than 96% of the isoolefin. For example, various embodiments may provide for conversion of 92% to 96% of the isoolefin, such as from 93% to 95% of the isoolefin (conversion is on a molar basis unless otherwise noted).

The operational flexibility of the fixed bed reactors may be limited, based on their size, catalyst content, and their ability to handle the exotherm. However, splitting of the feed according to embodiments herein may provide significant operational flexibility, as the CD column may readily handle additional isoolefin and the associated exotherm. Accordingly, systems described herein may be used to process feeds over a wide range of isoamylene content and/or over a wide range of feed rates.

Referring now to FIG. 1, a simplified flow diagram of processes for converting isoolefins to tertiary alkyl ethers is illustrated. A mixed hydrocarbon stream 10, such as a feedstock containing 50 wt % to 70 wt % isoamylene, may be mixed with an alcohol feed stream 12 to form a mixed feed 14. The alcohol feed stream 12 may include a fresh alcohol 16, such as a fresh methanol feed, for producing TAME, or ethanol, for producing TAEE, for example, as well as recycled alcohol 18.

The mixed feed stream 14 may be divided, such as by using flow tees and appropriate valving, into three portions 20, 22, 24. A first portion 20 of the mixed feed (isoamylene feed and alcohol) may be fed to a first reactor 28 containing an etherification catalyst. The isoamylene and alcohol may be reacted over the etherification catalyst at appropriate reaction conditions to convert at least a portion of the isoamylene and alcohol to tertiary amyl alkyl ether. Following conversion, a reactor effluent 30 may be recovered, the effluent including the ether product as well as unreacted hydrocarbons (reaction inerts in the isoamylene feed and unreacted isoamylene) and unreacted alcohols. Oxygenated byproducts, such as dimethyl ether, and oligomers, such as diisopentene, may also be formed.

The reactor effluent may then be divided into an effluent recycle portion 32 and an effluent portion 34. Effluent recycle portion 32 may be mixed with the first portion 20 of the mixed feed, such that the total mixed feed 26, including isoamylene feed, first reactor effluent portion 32, and alcohol, is fed to the first reactor 28.

Effluent portion 34 may be mixed with a second portion 22 of the mixed feed, forming a mixed feed 36 that may be fed to second reactor 38. Second reactor 38 may also contain an etherification catalyst, which may be the same or different from that contained in first reactor 28. The isoamylene and alcohol in the feed to second reactor 38 may be reacted over the etherification catalyst at appropriate reaction conditions to convert at least a portion of the isoamylene and alcohol to tertiary amyl alkyl ether. Following conversion, a reactor effluent 40 may be recovered, the effluent including the ether product as well as unreacted hydrocarbons (reaction inerts in the isoamylene feed and unreacted isoamylene) and unreacted alcohols. Oxygenated byproducts, such as dimethyl ether, and oligomers, such as diisopentene, may also be formed.

Flow control may be provided to control the concentration of the isoamylene in the total feed (streams 26, 36) fed to each of first and second reactors. In some embodiments, the flow of the respective streams may be controlled such that a concentration of isoamylene fed to the first and second reactors is less than 30 wt %, such as less than 28 wt %, such as less than 25 wt %, less than 20 wt %, or less than 15 wt %. In some embodiments, the isoamylene concentration in one or both of streams 26, 36 may be controlled to be within the range of 20 wt % to 30 wt %. Flow rates of streams 20, 22, 32, and 34, may be adjusted based on one or more of the following: concentration of isoamylene in the isoamylene feedstock 10, a feed rate of the alcohol, and a desired space velocity within reactors 28, 38, among other factors, to meet the desired isoamylene content of the total reactor feeds 26, 36.

A third portion 24 of the mixed feed may be mixed with the second reactor effluent 40 and fed to CD Column 42, which may contain a bed of catalytic distillation structures containing an etherification catalyst. Feed to the column may be provided, in some embodiments, to a feed tray located below the etherification catalyst bed. Concurrently in the CD column 42: (i) the alcohol and isoamylene may distill upward into the etherification catalyst, reacting to form additional tertiary amyl alkyl ether; (ii) light hydrocarbon inerts and unreacted isoolefin and alcohol may distill upward and be recovered as an overheads product 44; and, (iii) the product ether may distill downward in the column to be recovered as a bottoms product 50.

The overheads product 44 may then be forwarded to an alcohol recovery system 46 to separate unreacted alcohol 18 from inert and unreacted hydrocarbons contained in the isoamylene feed 10. The inert and unreacted hydrocarbons may be recovered as a raffinate fraction 48. The recovered alcohol 18 may be recycled for admixture with fresh isoamylene feed 10, and fresh alcohol feed 16, as described above.

Figure 2:
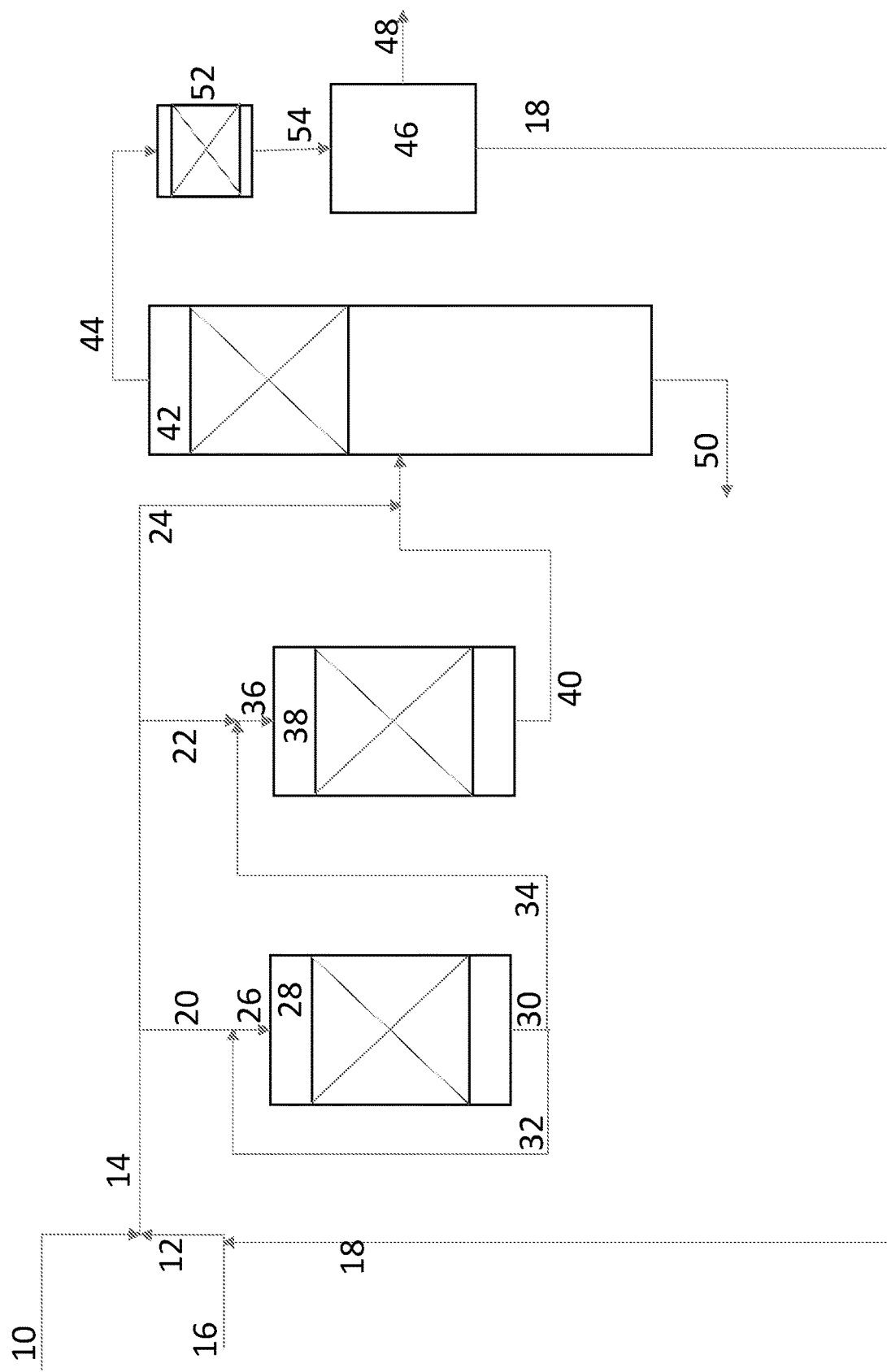
FIG. 2 is a simplified flow diagram of a process according to one or more embodiments disclosed herein.

Referring now to FIG. 2, a simplified flow diagram of processes for converting isoolefins to tertiary alkyl ethers is illustrated, where like numerals represent like parts. In the embodiments of FIG. 2, the olefins and alcohols may be processed similar to that as described above with respect to FIG. 1. Following conversion and separation in CD column 42, the overheads fraction 44 recovered may be fed to a finishing reactor 52, containing an etherification catalyst, which may be the same or different than the etherification catalysts contained in the other reactors. Finishing reactor 52 may be used to convert unreacted isoolefin and alcohols contained in the overheads fraction 44, prior to feed of the finishing reactor effluent 54 to alcohol recovery unit 46 for separation and recovery of the unreacted alcohols 18 from the hydrocarbons 48, such as a C5 Raffinate II product, in the overheads fraction.

Figure 3:
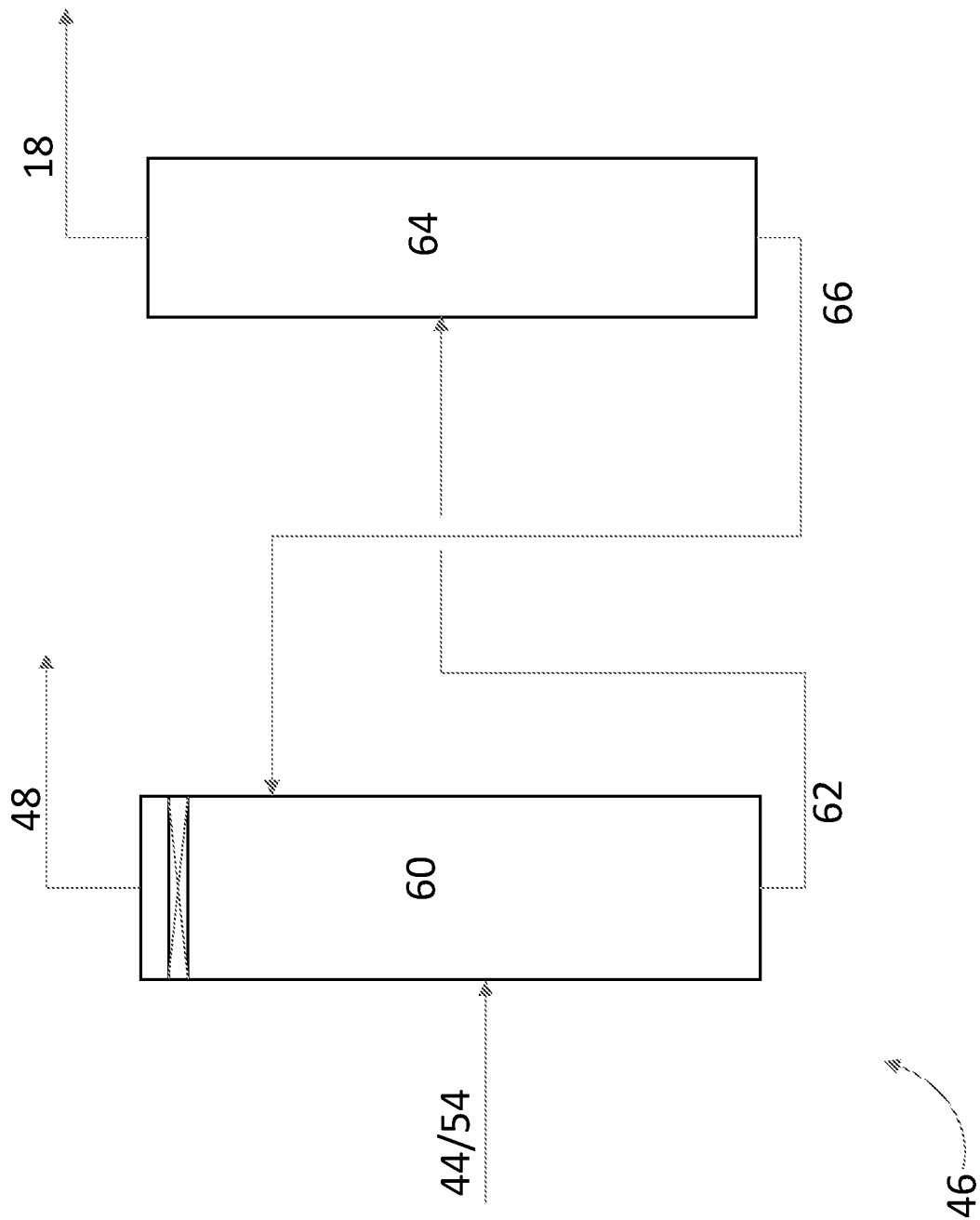
FIG. 3 is a simplified flow diagram of an alcohol recovery unit useful in processes according to one or more embodiments disclosed herein.

Referring now to FIG. 3, a simplified flow diagram of an alcohol recovery system 46 useful in embodiments of processes herein is illustrated, where like numerals represent like parts. The overheads fraction 44/54 may be fed to a wash column 60, absorbing the methanol with an absorbent 66, such as water. The undissolved hydrocarbons may be recovered as an overheads fraction 48 from the wash column, and the absorbent-alcohol mixture may be recovered as a bottoms fraction 62. Bottoms fraction 62 may then be fed to distillation column 64 for separation of the absorbent from the alcohol. The lean absorbent may be recovered from column 64 as a bottoms fraction 66 and fed to column 60 as the wash liquid. The alcohol may be recovered from column 64 as an overheads fraction 18, which may be recycled to the reaction zone (reactors 28, 38, 42). While described herein as a two-column system for separating the alcohol from the hydrocarbons, other alcohol recovery systems may also be used.

As described above, embodiments herein advantageously divide an isoolefin feed between multiple fixed bed reactors and a CD column. One advantage of the process schemes presented herein compared to prior art etherification processes is the ability of the scheme to process a higher concentration feedstock that allows for a high production capacity with smaller plant sizing. Embodiments herein are able to utilize a higher concentration feedstock compared to prior practice. The implementation of a bypass line around portions of the fixed bed reactors allows for regulation of the fixed bed reactor inlet concentrations, allowing both a high conversion and control of the exotherm associated with the etherification reaction.

Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed as new and desired to be protected by Letters Patent of the United States is:

1. A process for producing tertiary amyl alkyl ether, the process comprising:
    providing a mixed hydrocarbon feed containing a mixture of C5 hydrocarbons, wherein the mixed hydrocarbon feed contains greater than 50 wt % isoamylene;
    dividing the mixed hydrocarbon feed into three portions, including a first isoamylene feed portion, a second isoamylene feed portion, and a third isoamylene feed portion;
    feeding the first isoamylene feed portion, alcohol, and a first portion of a first reactor effluent to a first reactor;
    in the first reactor, reacting the alcohol with isomaylene over an etherification catalyst to form tertiary amyl alkyl ether and recovering a first reactor effluent;
    dividing the first reactor effluent into the first portion of the first reactor effluent, a second portion of the first reactor effluent, and recycling the first portion of the first reactor effluent to the first reactor;
    feeding the second portion of the first reactor effluent, alcohol, and the second isoamylene feed portion to a second reactor;
    in the second reactor, reacting the alcohol with isomaylene over an etherification catalyst to form tertiary amyl alkyl ether and recovering a second reactor effluent;
    feeding the second reactor effluent, alcohol, and the third isoamylene feed portion to a catalytic distillation column;
    in the catalytic distillation column:
        reacting isoamylene and alcohol over an etherification catalyst to form tertiary amyl alkyl ether;
        separating the tertiary amyl alkyl ether from unreacted alcohol, unreacted isoamylene, and other C5 hydrocarbons contained in the mixed hydrocarbon feed;
        recovering the tertiary amyl alkyl ether from the catalytic distillation column as a bottoms fraction; and
        recovering the unreacted alcohol, unreacted isoamylene, and other C5 hydrocarbons contained in the mixed hydrocarbon feed as an overheads fraction.

2. The process of claim 1, further comprising maintaining isoamylene in a total feed to the first reactor at a concentration of less than 28 wt %.

3. The process of claim 1, further comprising maintaining isoamylene in a total feed to the second reactor at a concentration of less than 28 wt %.

4. The process of claim 1, further comprising mixing an alcohol feed stream and/or an alcohol recycle stream with the mixed feed stream prior to separating the mixed feed stream into the three portions.

5. The process of claim 1, further comprising separating the overheads fraction to recover an alcohol recycle fraction and a hydrocarbon raffinate fraction.

6. The process of claim 5, further comprising feeding the alcohol recycle fraction to one or more of the first reactor, the second reactor, and the catalytic distillation column.

7. The process of claim 1, further comprising feed the overhead fraction to a finishing reactor, reacting the unreacted alcohol and unreacted isoamylene over an etherification catalyst to form additional tertiary amyl alkyl ether.

* * * * *